(12) United States Patent
Karube et al.

(10) Patent No.: US 9,452,958 B2
(45) Date of Patent: Sep. 27, 2016

(54) PROCESS FOR PRODUCING FLUORINE-CONTAINING OLEFIN

(71) Applicant: DAIKIN INDUSTRIES, LTD., Osaka (JP)

(72) Inventors: Daisuke Karube, Osaka (JP); Takehiro Chaki, Osaka (JP); Masami Nishiumi, Osaka (JP); Takashi Shibanuma, Osaka (JP); Masashi Arai, Osaka (JP)

(73) Assignee: DAIKIN INDUSTRIES, LTD., Osaka (JP)

(*) Notice: Subject to any disclaimer, the term of this patent is extended or adjusted under 35 U.S.C. 154(b) by 0 days.

(21) Appl. No.: 14/358,101

(22) PCT Filed: Jan. 24, 2013

(86) PCT No.: PCT/JP2013/052120
§ 371 (c)(1),
(2) Date: May 14, 2014

(87) PCT Pub. No.: WO2013/111911
PCT Pub. Date: Aug. 1, 2013

(65) Prior Publication Data
US 2014/0303412 A1    Oct. 9, 2014

Related U.S. Application Data

(60) Provisional application No. 61/703,951, filed on Sep. 21, 2012, provisional application No. 61/653,006, filed on May 30, 2012, provisional application No. 61/590,500, filed on Jan. 25, 2012.

(51) Int. Cl.
| | |
|---|---|
| C07C 17/20 | (2006.01) |
| C07C 17/25 | (2006.01) |
| B01J 37/03 | (2006.01) |
| B01J 37/06 | (2006.01) |
| B01J 37/26 | (2006.01) |
| B01J 23/02 | (2006.01) |
| B01J 23/26 | (2006.01) |
| B01J 27/132 | (2006.01) |
| B01J 37/00 | (2006.01) |
| B01J 37/02 | (2006.01) |
| B01J 35/00 | (2006.01) |

(52) U.S. Cl.
CPC ............ *C07C 17/20* (2013.01); *B01J 23/02* (2013.01); *B01J 23/26* (2013.01); *B01J 27/132* (2013.01); *B01J 37/009* (2013.01); *B01J 37/0201* (2013.01); *B01J 37/031* (2013.01); *B01J 37/06* (2013.01); *B01J 37/26* (2013.01); *C07C 17/206* (2013.01); *C07C 17/25* (2013.01); *B01J 35/002* (2013.01); *B01J 2523/00* (2013.01); *Y02P 20/582* (2015.11)

(58) Field of Classification Search
CPC .......................... C07C 17/25; C07C 17/206
See application file for complete search history.

(56) References Cited

U.S. PATENT DOCUMENTS

| 5,895,825 | A | * | 4/1999 | Elsheikh et al. .............. 570/167 |
| 7,704,918 | B2 | * | 4/2010 | Adzic et al. .................. 502/327 |
| 2007/0027348 | A1 | | 2/2007 | Quan et al. |

FOREIGN PATENT DOCUMENTS

| AU | 682225 | 6/1995 |
| JP | 2004-043410 | 2/2004 |
| WO | 2010/123154 | 10/2010 |
| WO | 2012/098422 | 7/2012 |

OTHER PUBLICATIONS

Sigma "Vanadium salts", 2016, p. 1.*
Endmemo "Vanadium perchlorate", 2016, p. 1.*
International Search Report issued May 27, 2013 in International (PCT) Application No. PCT/JP2013/052120.
Karamullaoglu et al., "Oxidative dehydrogenation of ethane and isobutane with chromium—vanadium—niobium mixed oxide catalysts", Chemical Engineering and Processing, vol. 41, No. 4, 2002, pp. 337-347.
Zhu et al., "Aliovalent-substituted chromium-based catalysts for the hydrofluorination of tetrachloroethylene", Journal of Catalysis, vol. 219, 2003, pp. 8-16.

* cited by examiner

*Primary Examiner* — Jafar Parsa
*Assistant Examiner* — Medhanit Bahta
(74) *Attorney, Agent, or Firm* — Wenderoth, Lind & Ponack, L.L.P.

(57) ABSTRACT

This invention provides a process for producing a fluoroolefin comprising reacting, in a vapor phase, a fluorinating agent and a chlorine-containing alkene or a chlorine-containing alkane in the presence of at least one catalyst selected from the group consisting of chromium oxide containing a Group 5 element and fluorinated chromium oxide containing a Group 5 element. According to the process of the present invention, the target fluoroolefin can be obtained with high starting material conversion and good selectivity.

13 Claims, No Drawings

PROCESS FOR PRODUCING FLUORINE-CONTAINING OLEFIN

TECHNICAL FIELD

The present invention relates to a process for producing fluorine-containing olefin.

BACKGROUND ART

Fluoroolefins represented by formula: $CF_3(CX_2)_n CF=CH_2$, formula: $CF_3(CX_2)_n CH=CHF$, or the like, are compounds having a useful structure as various functional materials, solvents, refrigerants, blowing agents, and the monomers for functional polymers or starting materials of such monomers. For example, fluoroolefins are used as monomers for modifying an ethylene-tetrafluoroethylene copolymer. Further, of the fluoroolefins mentioned above, the compound represented by $CF_3CF=CH_2$ (HFO-1234yf) and the compound represented by $CF_3CH=CHF$ (HFO-1234ze) have recently gained attention, as they offer promising prospects as refrigerants of low global warming potential.

As processes for producing the fluoroolefins represented by the formulae above, many processes have been reported in which a starting material chlorine-containing alkane or chlorine-containing alkene having the same number of carbon atoms as that of a target fluoroolefin is reacted with a fluorinating agent such as an anhydrous hydrogen fluoride in the presence of a catalyst. In these processes, chromium oxide catalysts, antimony catalysts, etc., are used as catalysts. In particular, chromium oxide catalysts are widely used because of ease of industrial use (e.g., Patent Literature 1).

However, the conversion of a starting material is not particularly high when a chromium oxide catalyst is used; in this case, a huge reaction facility is necessary to obtain a sufficient production amount per unit time, and it is uneconomical in view of facility cost and operation cost.

Moreover, when a chromium oxide catalyst is used, several byproducts, which sometimes cannot be converted to target products, are generated, causing problems such as a reduction in the yield of target fluoroolefin, complications in a purification step, rise in the costs of the facility used in the purification step, and the like. Further, when a chromium oxide catalyst is used, since the activity is significantly deteriorated depending on the conditions, use of an activity deterioration inhibitor, which is not necessary in conventional reactions, is needed, which becomes one of the causes of the rise in costs due to an increase of byproducts and a complicated production step.

CITATION LIST

Patent Literature

PTL 1: WO 2010/123154

SUMMARY OF INVENTION

Technical Problem

The present invention is made in light of the current status of the aforementioned technical field, and a main object is to provide a process for efficiently producing fluoroolefins using a catalyst, which can be easily used in the industrial field, by improving the conversion of a starting material; inhibiting the generation of impurities, which causes problems in separation and yield; and further inhibiting deterioration of catalyst activity.

Solution to Problem

The present inventors conducted extensive research to achieve the above object. As a result, they found the following. When chromium oxide containing a Group 5 element or fluorinated chromium oxide containing a Group 5 element is used as a catalyst to produce a fluoroolefin by reacting a fluorinating agent with a chlorine-containing alkane represented by a specific formula or a chlorine-containing alkene represented by a specific formula, which is used as a starting material, the conversion of the starting material is improved, and the selectivity of the target fluoroolefin is increased, which allows efficient production of fluoroolefin. In particular, when chromium oxide containing two or more elements selected from the group consisting of V, Nb, and Ta, or fluorinated chromium oxide containing two or more elements selected from the group consisting of V, Nb, and Ta is used as a catalyst, the conversion of the starting material is further improved, the selectivity of the target fluoroolefin is increased, and catalyst deterioration can be inhibited; thus, a fluoroolefin can be efficiently produced.

The present invention was accomplished as a result of further research based on these findings.

Specifically, the present invention offers the following process for producing a fluoroolefin.

Item 1. A process for producing a fluoroolefin represented by formula (6): $CF_3(CF_2)_n CA=CHB$, wherein one of A and B is F and the other is H, n is an integer of 0 to 2, proviso that n is 0 when a chlorine-containing alkene represented by formula (5) is used as a starting material, comprising reacting, in a vapor phase, a fluorinating agent and at least one chlorine-containing compound in the presence of at least one catalyst selected from the group consisting of chromium oxide containing a Group 5 element and fluorinated chromium oxide containing a Group 5 element, the at least one chlorine-containing compound being selected from the group consisting of a chlorine-containing alkane represented by formula (1): $CX_3(CX_2)_n CClYCH_2Z$, wherein X is independently F or Cl, Y is H or F, when Y is H, Z is Cl or F, and when Y is F, Z is H, and n is an integer of 0 to 2; a chlorine-containing alkane represented by formula (2): $CX_3(CX_2)_n CH_2CHX_2$, wherein X is independently F or Cl, and at least one X is Cl, and n is an integer of 0 to 2; a chlorine-containing alkene represented by formula (3): $CX_3(CX_2)_n CCl=CH_2$, wherein X is independently F or Cl, and n is an integer of 0 to 2; a chlorine-containing alkene represented by formula (4): $CX_3(CX_2)_n CH=CHX$, wherein X is independently F or Cl, and at least one X is Cl, and n is an integer of 0 to 2; and a chlorine-containing alkene represented by formula (5): $CH_2XCCl=CX_2$, wherein X is independently F or Cl.

Item 2. The process for producing a fluoroolefin according to Item 1, wherein the Group 5 element contained in the catalyst is at least one element selected from the group consisting of V and Nb.

Item 3. The process for producing a fluoroolefin according to Item 1, wherein the Group 5 element contained in the catalyst is two or more elements selected from the group consisting of V, Nb, and Ta.

Item 4. The process for producing a fluoroolefin according to Item 1, wherein the Group 5 element in the catalyst is contained in an amount of 0.1 to 30 atom % based on the total amount of Cr and the Group 5 element in the catalyst.

Item 5. The process for producing a fluoroolefin according to Item 1, wherein the catalyst contains vanadium in an amount of 0.1 to 6 atom % based on the total amount of Cr and the Group 5 element in the catalyst.

Item 6. The process for producing a fluoroolefin according to Item 1, wherein the fluorinating agent is anhydrous hydrogen fluoride.

Item 7. The process for producing a fluoroolefin according to Item 1, wherein the chlorine-containing compound used as a starting material is at least one member selected from the group consisting of a chlorine-containing alkane represented by formula (1): $CX_3(CX_2)_n CClYCH_2Z$, a chlorine-containing alkene represented by formula (3): $CX_3(CX_2)_n CCl=CH_2$, and a chlorine-containing alkene represented by formula (5): $CH_2XCCl=CX_2$, and the fluoroolefin obtained is a compound represented by formula (6-1): $CF_3(CF_2)_n CF=CH_2$, or a mixture of a compound represented by formula (6-1) and a compound represented by formula (6-2): $CF_3(CF_2)_n CH=CHF$, wherein n in each of formula (6-1) and formula (6-2) is an integer of 0 to 2, proviso that n is 0 when the chlorine-containing alkene represented by formula (5) is used as a starting material.

Item 8. The process for producing a fluoroolefin according to Item 7, wherein the chlorine-containing compound used as a starting material is at least one member selected from the group consisting of $CF_3CHClCH_2Cl$ (HCFC-243db), $CF_3CFClCH_3$ (HCFC-244bb), $CCl_3CCl=CH_2$ (HCO-1230xf), $CF_3CCl=CH_2$ (HCFO-1233xf), and $CH_2ClCCl=CCl_2$ (HCO-1230xa), and the fluoroolefin obtained is $CF_3CF=CH_2$ (HFO-1234yf) or a mixture of $CF_3CF=CH_2$ (HFO-1234yf) and $CF_3CH=CHF$ (HFO-1234ze).

Item 9. The process for producing a fluoroolefin according to Item 1, wherein the chlorine-containing compound used as a starting material is at least one member selected from the group consisting of a chlorine-containing alkane represented by formula (2): $CX_3(CX_2)_n CH_2CHX_2$ and a chlorine-containing alkene represented by formula (4): $CX_3(CX_2)_n CH=CHX$, and the fluoroolefin obtained is a fluoroolefin represented by formula (6-2): $CF_3(CF_2)_n CH=CHF$, wherein n is an integer of 0 to 2.

Item 10. The process for producing a fluoroolefin according to Item 9, wherein the chlorine-containing compound used as a starting material is at least one member selected from the group consisting of $CCl_3CH=CHCl$ (HCO-1230zd) and $CF_3CH=CHCl$ (HCFO-1233zd), and the fluoroolefin obtained is $CF_3CH=CHF$ (HFO-1234ze).

Item 11. The process for producing a fluoroolefin according to Item 10, wherein the chlorine-containing compound used as a starting material is $CF_3CH=CHCl$ (HCFO-1233zd) and the fluoroolefin obtained is $CF_3CH=CHF$ (HFO-1234ze).

Item 12. The process for producing a fluoroolefin according to Item 1, wherein reaction is performed in the presence of oxygen, chlorine, or both oxygen and chlorine.

Item 13. The process for producing a fluoroolefin according to Item 12, wherein the reaction is performed in the presence of oxygen in an amount of 0.001 to 0.2 mol per mol of the chlorine-containing compound used as a starting material.

Item 14. A catalyst for producing a fluoroolefin by fluorination of a chlorine-containing alkene or a chlorine-containing alkane, the catalyst comprising at least one compound selected from the group consisting of chromium oxide containing a Group 5 element and fluorinated chromium oxide containing a Group 5 element.

Item 15. The catalyst for producing a fluoroolefin by fluorination of a chlorine-containing compound according to Item 14, wherein the Group 5 element is two or more elements selected from the group consisting of V, Nb, and Ta.

Hereinbelow, the process for producing a fluoroolefin of the present invention is specifically explained.

Starting Material

In the present invention, at least one chlorine-containing compound selected from the group consisting of a chlorine-containing alkane represented by formula (1): $CX_3(CX_2)_n CClYCH_2Z$, wherein X is independently F or Cl, Y is H or F, when Y is H, Z is Cl or F, and when Y is F, Z is H, n is an integer of 0 to 2; a chlorine-containing alkane represented by formula (2): $CX_3(CX_2)_n CH_2CHX_2$, wherein X is independently F or Cl, and at least one X is Cl, and n is an integer of 0 to 2; a chlorine-containing alkene represented by formula (3): $CX_3(CX_2)_n CCl=CH_2$, wherein X is independently F or Cl, and n is an integer of 0 to 2; a chlorine-containing alkene represented by formula (4): $CX_3(CX_2)_n CH=CHX$, wherein X is independently F or Cl, and at least one X is Cl, and n is an integer of 0 to 2; and a chlorine-containing alkene represented by formula (5): $CH_2XCCl=CX_2$, wherein X is independently F or Cl, is used as a starting material.

By reacting such a chlorine-containing compound as a starting material with a fluorinating agent in the presence of a specific catalyst according to the conditions described below, a fluoroolefin represented by formula (6): $CF_3(CF_2)_n CA=CHB$, wherein one of A and B is F and the other is H, and n is an integer of 0 to 2, proviso that n is 0 when the chlorine-containing alkene represented by formula (5) is used as a starting material, can be obtained with high selectivity and high starting material conversion.

Of the chlorine-containing compounds represented by formulae (1) to (5), compounds in which the number of carbon atoms is 3, i.e., n is 0 are preferable because they have an appropriate boiling point to perform a vapor phase reaction. Preferable examples of the compounds in which n is 0 include $CCl_3CHClCH_2Cl$ (HCC-240db), $CF_3CHClCH_2Cl$ (HCFC-243db), $CF_3CFClCH_3$ (HCFC-244bb), and the like as the chlorine-containing alkane represented by formula (1); $CCl_3CH_2CHCl_2$ (HCC-240fa), $CF_3CH_2CHCl_2$ (HCFC-243fa), and the like as the chlorine-containing alkane represented by formula (2); $CCl_3CCl=CH_2$ (HCO-1230xf), $CF_3CCl=CH_2$ (HCFO-1233xf), and the like as the chlorine-containing alkene represented by formula (3); $CCl_3CH=CHCl$ (HCO-1230zd), $CF_3CH=CHCl$ (HCFO-1233zd), and the like as the chlorine-containing alkene represented by formula (4); and $CH_2ClCCl=CCl_2$ (HCO-1230xa), and the like as the chlorine-containing alkene represented by formula (5). Of these compounds, $CF_3CCl=CH_2$ (HCFO-1233xf) and $CF_3CH=CHCl$ (HCFO-1233zd) are particularly preferable. HCFO-1233xf is a well-known compound, and can be easily obtained, for example, by adding chlorine to 3,3,3-trifluoro-1-propene to form HCFC-243db, and then subjecting the HCFC-243db to dehydrochlorination with alkali or the like.

In the present invention, the aforementioned starting materials can be used singly, or in a combination of two or more.

Catalyst

In the process for producing fluoroalkene of the present invention, as a catalyst, at least one member selected from the group consisting of chromium oxide containing a Group 5 element and fluorinated chromium oxide containing a Group 5 element can be used. In this case, it is considered that the Group 5 element contained in the catalyst has an excellent effect of substituting a starting material chlorine atom, particularly, a chlorine atom on olefin, to a fluorine atom in the presence of a fluorinating agent. By reacting the aforementioned starting material and a fluorinating agent in the presence of such a specific catalyst, the target fluoroolefin can be produced with high starting material conversion and high selectivity.

In chromium oxide containing a Group 5 element and fluorinated chromium oxide containing a Group 5 element, it is only necessary that at least one Group 5 element is simultaneously present with chromium oxide or fluorinated chromium oxide, and the existential state of the Group 5 element is not particularly limited. For example, the Group 5 element may be unevenly distributed on the surface of chromium oxide or fluorinated chromium oxide, or the Group 5 element may be uniformly mixed with chromium oxide or fluorinated chromium oxide. In these cases, the Group 5 element may be present as a metal or in the state of oxide, oxy fluoride, or the like. Further, the Group 5 element may be partially or wholly combined with a chromium metal to form a complex oxide. Chromium oxide or fluorinated chromium oxide containing a Group 5 element may be in a crystalline state or an amorphous state, and preferably a crystalline state. The mixture of chromium oxide in a crystalline state and chromium oxide in an amorphous state can be also used.

Examples of the Group 5 elements include vanadium, niobium, tantalum, and the like. Vanadium, niobium, and the like are preferable because they are easily available and exhibit high performance. In particular, niobium is preferable. The Group 5 elements may be contained singly, or in a combination of two or more.

In the catalyst used in the present invention, the Group 5 element is preferably present in a quadrivalent or pentavalent state. In this case, as a starting material for producing a catalyst, a compound containing 0 to trivalent Group 5 element may be used, and the Group 5 element can be oxidized in the production step of the catalyst to attain a quadrivalent to pentavalent state.

In the present invention, at least one member selected from the group consisting of chromium oxide that contains two or more elements selected from the group consisting of V, Nb, and Ta among the Group 5 elements, and fluorinated chromium oxide that contains two or more elements selected from the group consisting of V, Nb, and Ta among the Group 5 elements is preferably used as a catalyst. Each of the V, Nb, and Ta contained in the chromium oxide is considered to have excellent effect of substituting a starting material chlorine atom, particularly a chlorine atom on olefin to a fluorine atom in the presence of a fluorinating agent. For this reason, by reacting the aforementioned starting material and a fluorinating agent in the presence of a catalyst containing chromium oxide that contains two or more elements selected from the group consisting of V, Nb, and Ta, or fluorinated chromium oxide that contains two or more elements selected from the group consisting of V, Nb, and Ta, a target fluoroolefin can be formed at a higher starting material conversion and higher selectivity.

Chromium oxide containing two or more elements selected from the group consisting of V, Nb, and Ta may be an oxide in which chromium oxide is a base material and contains two or more metal elements selected from the group consisting of V, Nb, and Ta in addition to chromium. The chromium oxide may be in an amorphous state or crystalline state. The existential state of V, Nb, and Ta is not particularly limited, and V, Nb, and Ta may be present in the state of oxide, or supported on chromium oxide, which is used as a base material, in the state of an isolated individual metal or ion. In particular, it is preferable that at least part of V, Nb, and Ta form an oxide. When V, Nb, and/or Ta are present as an oxide in addition to Cr, they can be present as a various oxide such as chromium oxide, niobium oxide, vanadium oxide, tantalum oxide, CrV complex oxide, CrNb complex oxide, CrTa complex oxide, NbV complex oxide, NbTa complex oxide, VTa complex oxide, CrNbV complex oxide, CrNbTa complex oxide, and CrVTa complex oxide. Although these oxides may be in an amorphous state or crystalline state, a crystalline state is preferable. A mixture of an oxide in an amorphous state and an oxide in a crystalline state can also be used. Note that an oxide in a crystalline state in the present invention refers to an oxide having a crystallite size of about 2 nm or more, which is measurable by XRD.

In chromium oxide containing two or more elements selected from the group consisting of V, Nb, and Ta, it is particularly preferable that two or more elements selected from the group consisting of Cr, Nb, V, and Ta form at least one complex oxide, and that at least part of the complex oxide contained in the catalyst be crystallized.

Fluorinated chromium oxide containing two or more elements selected from the group consisting of V, Nb, and Ta may be formed by fluorinating amorphous or crystalline chromium oxide containing two or more elements selected from V, Nb, and Ta. In particular, a catalyst obtained by fluorinating a chromium oxide catalyst in which two or more elements selected from the group consisting of Cr, Nb, V, and Ta form at least one complex oxide is preferable, and a catalyst in which at least part of the complex oxide is crystallized is preferable.

The amount of the Group 5 element contained in the catalyst is not limited. Although the Group 5 element has an effect of improving the starting material conversion and the target material selectivity, there is a tendency of reducing selectivity when the amount to be added is overly large. For this reason, to maintain a high level of selectivity while exhibiting the effect of improvement in the conversion, the amount of the Group 5 element is preferably about 0.1 to 30 atom %, more preferably about 0.1 to 25 atom %, and even more preferably about 0.1 to 10 atom % based on the total amount of Cr and the Group 5 element in the catalyst. When the catalyst contains two or more elements selected from the group consisting of V, Nb, and Ta, the total amount of the elements may be within the aforementioned range.

When V (vanadium) is contained as the Group 5 element, because an overly large amount of V causes a tendency of decreasing the selectivity, the amount of V is preferably about 0.1 to 6 atom %, and more preferably about 0.1 to 5 atom % based on the total amount of Cr and the Group 5 element in the catalyst.

Production Process of Catalyst

The process for producing the catalyst explained above is not particularly limited. Examples of the process for producing chromium oxide containing a Group 5 element include a process comprising adding chromium oxide, or chromium hydroxide as a precursor of the chromium oxide, to a solution containing a Group 5 element to impregnate the Group 5 element, removing a solvent, and calcinating the residue (impregnation process); a process comprising precipitating Cr and a Group 5 element as hydroxide, ammonium salt, carbonate, hydrogencarbonate, etc., from a solution containing the Cr and the Group 5 element, and washing, drying, and then calcinating the precipitates (co-precipitation process); a process comprising subjecting a solution containing Cr and a Group 5 element to a hydrothermal synthesis reaction to precipitate the Cr and the Group 5 element from the solution, then calcinating the separated precipitates (hydrothermal synthesis process); a process comprising physically mixing salts containing Cr and a Group 5 element, oxides containing Cr and a Group 5 element, or the like using a mortar, etc., and, if necessary, calcinating the mixture (kneading process); etc. In addition, the following processes (chemical vapor deposition; CVD process; and the like) can be used, in which a metal salt of a Group 5 element with sublimability, such as niobium chloride, vanadium chloride, or tantalum chloride is physically mixed with chromium oxide using a mortar, etc., after which the mixture is heated to the sublimation temperature of the metal salt with sublimability and the sublimed metal salt is deposited on the chromium oxide, and if necessary, the metal salt is decomposed so that metal or metal oxide is supported on the chromium oxide.

Of these processes, typical processes are explained below in detail.

(a) Impregnation Process

First, an aqueous solution of chromium salt (chromium nitrate, chromium chloride, chromium alum, chromium sulfate, and chromium acetate) is mixed with aqueous ammonia to obtain precipitates of chromium hydroxide. For example, about 1 to 1.2 equivalents of 10% aqueous ammonia per equivalent of chromium nitrate is added dropwise to a 5.7% chromium nitrate aqueous solution to obtain precipitates of chromium hydroxide.

The obtained chromium hydroxide is immersed in a solution containing a Group 5 element, and then a solvent is evaporated while sufficiently stirring the solution, thus obtaining a solid in which the Group 5 element is impregnated in the chromium hydroxide. The solution containing a Group 5 element can be obtained by dissolving a soluble salt of a Group 5 element in a solvent such as water, alcohol, and an organic acid, e.g., carboxylic acid. As a method of evaporating a solvent after chromium hydroxide is immersed in a solution containing a Group 5 element, a method for heating the solution in a drying dish, etc. and a method for evaporating a solvent by heating the solution while reducing pressure using an evaporator can be used. The method can be suitably selected according to the properties such as the boiling point of the solvent.

Subsequently, the aforementioned solid is dried. Drying may be performed, for example, in air at about 70 to 200° C. for about 1 to 100 hours.

Next, the product is crushed to obtain powders, and if necessary, graphite is added in an amount of about 3 wt % or less to the powders. Pellets are formed with a tableting machine. The pellets have, for example, a diameter of about 3.0 mm and a height of about 3.0 mm.

Subsequently, the formed pellets are calcined under an inert atmosphere; for example, in nitrogen gas flow.

In this case, the calcination temperature is adjusted as necessary to control the crystallinity of chromium oxide containing a Group 5 element. For example, to obtain amorphous chromium oxide containing a Group 5 element, calcination may be performed at about 380 to 460° C. for about 1 to 5 hours.

Further, chromium hydroxide is prepared in the above process, and then calcined to form chromium oxide, after which the chromium oxide is immersed in a solution containing a Group 5 element to evaporate a solvent while stirring. Thereafter, precipitates are collected by filtration, and then calcined according to the aforementioned process.

By such a process, chromium oxide containing a Group 5 element can also be obtained.

(b) Coprecipitation Process

In the coprecipitation process, chromium oxide containing a Group 5 element can be obtained by performing precipitate formation, filtration, drying, and calcination in the same manner as in the impregnation process, except that a solution in which a salt of a Group 5 element is dissolved in addition to a chromium salt is used in place of a solution containing a chromium salt used in the production according to the impregnation process.

In this case, by optimizing the conditions of the precipitate formation step or the conditions of the calcination step, a chromium oxide catalyst containing a complex oxide that contains two or more elements selected from the group consisting of Cr and Group 5 elements can be obtained.

For example, in the precipitation formation step, a solution that contains salts of Group 5 elements in addition to a Cr salt is sufficiently stirred, and a buffer solution or/and alkaline liquid is added so that the solution is adjusted to a pH at which all of Cr and the Group 5 elements form precipitates such as hydroxides. Thereby, the precipitates such as hydroxides containing Cr and Group 5 elements are simultaneously formed. The precipitates are separated and collected from the liquid, and subjected to a drying step and a calcination step to obtain chromium oxide containing Group 5 elements. In addition, when the precipitates are hydroxides, each hydroxide randomly condenses, and thus the precipitates of complex oxides having a structure in which different metals are combined via oxygen atom can be produced. The precipitates are separated and collected from the liquid, and subjected to a drying step and a calcination step to obtain chromium oxide containing several complex oxides that contain two or more elements selected from the group consisting of Cr and Group 5 elements. In this case, by adjusting the conditions of the calcination step, chromium oxide that contains amorphous or crystalline complex oxides, or both amorphous and crystalline complex oxides can be obtained.

Although the alkali liquid used herein is not limited, aqueous solutions exhibiting alkalinity, such as a sodium hydroxide aqueous solution, potassium hydroxide aqueous solution, sodium hydrogencarbonate aqueous solution, potassium hydrogencarbonate aqueous solution, aqueous ammonia, urea solution, and the like, can be used.

To obtain an amorphous complex oxide according to a coprecipitation process, the precipitate of complex oxide obtained in the coprecipitation step may be collected by filtration, dried, and then calcined for 1 to 5 hours at 380 to 460° C. under an inert gas flow such as $N_2$ flow in the calcination step.

On the other hand, to obtain a chromium oxide containing a Group 5 element in which part or all of the complex oxide is crystallized, the calcination step may be conducted for about 1 to 5 hours at 350 to 1000° C. in air or under an atmosphere of a mixed gas of $N_2$ and $O_2$, which is adjusted to have a desired $O_2$ concentration.

(c) Hydrothermal Synthesis Process

A chromium oxide catalyst containing a complex oxide that contains two or more elements selected from the group consisting of Cr and Group 5 elements can also be produced by a hydrothermal synthesis process. For example, a solution in which at least one Group 5 element salt is dissolved in addition to a Cr salt is sealed in a pressurized sealed vessel, and heated at 180 to 400° C. for 20 to 200 hours. The generated precipitates are washed, if necessary, and subjected to the steps of separation, collection, drying, and calcination. Thus, a chromium oxide catalyst containing a complex oxide that contains two or more elements selected from the group consisting of Cr and Group 5 elements can be obtained. In this case, in the same manner as in the preparation process according to the coprecipitation process, chromium oxide containing an amorphous complex oxide or a complex oxide, at least part of which is crystallized, can be obtained by adjusting the conditions of the calcination step.

(d) Production Process of Fluorinated Chromium Oxide Containing Group 5 Element

The fluorinated chromium oxide containing a Group 5 element can be obtained by subjecting chromium oxide containing a Group 5 element to fluorination (HF treatment). The temperature of the fluorination treatment may be about 100 to 460° C. In this method, as the chromium oxide containing a Group 5 element, chromium oxide containing a complex oxide that contains two or more elements selected from the group consisting of Cr and Group 5 elements may be used, or chromium oxide that does not contain such an complex oxide may be used. In both cases, chromium oxide containing a Group 5 element may be amorphous, and may contain a complex oxide or chromium oxide, part or all of which is crystallized. Chromium oxide, at least part or all of which is crystallized is preferable in view of the stability of the catalyst and improvement in the selectivity.

Although the degree of fluorination is not limited, those having a fluorine content of about 1 to 30 wt % based on the total amount of fluorinated chromium oxide containing a Group 5 element can be preferably used.

Fluorination reaction of the chromium oxide containing a Group 5 element can be performed by supplying anhydrous hydrogen fluoride to a reactor in which the chromium oxide is filled, prior to performing the process of the present invention described below. Alternatively, by using the chromium oxide containing a Group 5 element as a catalyst in the fluorination reaction of a chlorine-containing compound, the chromium oxide can be gradually fluorinated during the reaction.

In both cases, in the chromium oxide after fluorination, Cr and a Group 5 element can be present in the form of oxide, fluoride, fluorinated oxide, and the like. A complex oxide containing two or more elements selected from the group consisting of Cr and Group 5 elements; a fluorinated complex oxide in which the complex oxide is partially fluorinated; etc., may be present. The fluorinated complex oxide may be amorphous, or at least part of the fluorinated complex oxide may be crystallized.

Note that, even when the catalyst prior to fluorination treatment does not contain a complex oxide, a complex oxide containing two or more elements selected from the group consisting of Cr and Group 5 elements can be formed during fluorination reaction of the catalyst prior to performing the process of the present invention, or during fluorination reaction of a chlorine-containing compound according to the process of the present invention. Catalysts, which are in an amorphous state prior to fluorination, may sometimes be partially or wholly crystallized during fluorination of the catalyst or fluorination reaction of a chlorine-containing compound. In the present invention, such catalysts can also effectively be used.

Reaction Method

In the present invention, the above-mentioned starting compound and fluorinating agent may be reacted in a vapor phase in the presence of at least one catalyst selected from the group consisting of the above-mentioned chromium oxide containing a Group 5 element, and fluorinated chromium oxide containing a Group 5 element.

Usable fluorinating agents are fluorine gas, anhydrous hydrogen fluoride, etc.; anhydrous hydrogen fluoride is preferred.

In a method of reacting the starting compound and the fluorinating agent in a vapor phase, the starting compound and the fluorinating agent may be in a gaseous state when the starting compound and the fluorinating agent are brought into contact with the catalyst. When the starting compound and the fluorinating agent are supplied, they may be in a liquid state. For example, when the starting compound is liquid at room temperature and normal pressure, the starting compound is vaporized by a vaporizer (vaporization region), then allowed to pass through a preheating region, and supplied to a mixing region in which the starting compound is brought into contact with the catalyst. Thus, the reaction can be carried out in a vapor phase. Alternatively, the starting compound is supplied to a reactor in a liquid state, while a catalyst layer placed in the reactor is heated above the vaporization temperature of the starting compound. When the starting compound arrives at a region for reaction with the fluorinating agent, the starting compound is vaporized and reacted.

The proportion of the fluorinating agent and the starting compound to be introduced is not particularly limited. However, when the amount of the fluorinating agent is overly low, the conversion of the starting compound tends to decrease. In contrast, when the proportion of the fluorinating agent is overly high, productivity is reduced because the amount of the fluorinating agent removed increases after the reaction. From these viewpoints, when anhydrous hydrogen fluoride is used as the fluorinating agent, the amount of anhydrous hydrogen fluoride is generally preferably 1 mol or more, more preferably 3 mol or more, still more preferably 5 mol or more, and particularly preferably about 5 to 20 mol, per mol of the starting compound.

A specific example of the embodiment of the method of the present invention is a method in which the above-mentioned catalyst is placed in a tubular flow-type reactor, and a chlorine-containing compound, which is used as a starting material, and the fluorinating agent are introduced into the reactor.

The reactor is preferably one made of a material resistant to the corrosive action of hydrogen fluoride, such as Hastelloy, Inconel, or Monel.

The above-mentioned starting material may be directly supplied to the reactor; or nitrogen, helium, argon, or another gas that is inert to the starting material and catalyst may be allowed to coexist. The concentration of the inert gas may be about 0 to 80 mol % based on the amounts of the inert gas and the gas components introduced into the reactor, i.e., the chlorine-containing compound and the fluorinating agent.

Moreover, in the method of the present invention, the reaction is optionally performed in the presence of one or both of molecular chlorine and oxygen, thereby preventing a decrease in catalytic activity, and enabling production of the target fluoroolefin continuously for a long period of time and with a high selectivity.

Although the method of performing the reaction in the presence of molecular chlorine and/or oxygen is not particularly limited, one or both of molecular chlorine and oxygen may be generally supplied to the reactor together with the chlorine-containing compound used as a starting material.

The amount of molecular chlorine supplied is preferably about 0.001 to 0.05 mol, and more preferably about 0.002 to 0.03 mol, per mol of the chlorine-containing compound used as a starting material.

The amount of oxygen supplied is, although not particularly limited, preferably about 0.001 mol or more, and more preferably about 0.001 to 0.3 mol, per mol of the chlorine-containing compound used as a starting material.

As for the catalyst containing vanadium as the Group 5 element, as described above, in order to achieve the effect of improving the starting material conversion while maintaining high selectivity, the vanadium content is preferably about 0.1 to 6 atom %, and more preferably about 0.1 to 5 atom %, based on the total amount of Cr and the Group 5 element in the catalyst. When a catalyst having a vanadium content within this range is used, the effect of preventing degradation of the catalyst can be sufficiently exhibited by supplying oxygen in an amount as relatively small as about 0.001 to 0.1 mol per mol of the chlorine-containing compound used as a starting material. Accordingly, problematic reduction in yield caused by the presence of excess oxygen can also be avoided. In the case of a catalyst having a vanadium content exceeding 3 atom % based on the total amount of Cr and the Group 5 element, selectivity tends to decrease as the oxygen content increases. Therefore, when such a catalyst having a vanadium content exceeding 3 atom % is used, the amount of oxygen supplied is preferably about 0.001 to 0.05 mol, and more preferably about 0.001 to 0.02 mol, per mol of the starting compound, from the viewpoint of preventing a decrease in selectivity.

Moreover, in the case of using a catalyst having a vanadium content of about 0.1 to 5 atom %, preferably about 0.1 to 3 atom %, and more preferably about 0.1 to 1 atom %, based on the total amount of Cr and the Group 5 element, the conversion can be maintained at a high level, and selectivity decrease can be prevented, within the above-mentioned oxygen supply range (about 0.001 to 0.1 mol per mol of the starting compound); however, even if the amount of oxygen supplied is as low as about 0.001 to 0.05 mol, and preferably about 0.001 to 0.02 mol, the decrease in conversion can be prevented, and high selectivity can be maintained.

The composition, specific surface area, metal valence, and other properties of the catalyst can be analyzed by generally used analytical methods. For example, but not limited to, the composition can be analyzed by SEM or an atomic absorption spectrometry; the specific surface area can be analyzed by a BET method; and the metal valence can be analyzed by XPS.

In addition, according to the method of the present invention, when the chlorine-containing compound used as a starting material and the fluorinating agent are reacted in a vapor phase while controlling the moisture content of the reaction system to a low level, a decrease in catalytic activity is prevented, resulting in production of the target fluoroolefin continuously for a long period of time and with a high yield. In this case, the moisture content of the reaction system is preferably 300 ppm or less, and more preferably 100 ppm or less, based on the weight of the chlorine-containing compound used as a starting material.

The moisture content of the reaction system refers to the amount of moisture present during the reaction conducted by bringing the chlorine-containing compound and the fluorinating agent into contact with the catalyst. More specifically, the moisture content refers to the total amount of moisture contained in the chlorine-containing compound as a starting material and the fluorinating agent, and moisture contained in the optional components, such as molecular chlorine, oxygen, and inert gas.

The method of reducing the moisture content of the reaction system is not particularly limited, and the chlorine-containing compound as a starting material, hydrogen fluoride, and other additives may be dehydrated by a known method before use in the reaction. For example, these components are subjected to the reaction after dehydration, or dehydrated and continuously supplied to the reaction system. Such methods can be suitably applied.

Regarding the reaction temperature, an overly low temperature results in a great reduction in starting material conversion, while an overly high temperature leads to an increase in the production of by-product impurities and a decrease in selectivity, and may further result in catalyst degradation. From these viewpoints, the reaction temperature is preferably about 200° C. to 550° C., and more preferably about 250° C. to 380° C.

The pressure during the reaction is, although not particularly limited, preferably in the range of atmospheric pressure to 3 MPa, and more preferably in the range of atmospheric pressure to about 0.3 MPa. When the pressure during the reaction is increased, the conversion of the starting material may be enhanced; however, an overly high pressure is not preferable, because safety and economic risks are increased, and the selectivity of the desired product may be reduced.

Although the reaction time is not particularly limited, for example, contact time $W/F_0$ represented by the ratio of the amount of catalyst supplied W (g) to the total flow of the starting material gas introduced into the reaction system $F_0$ (flow rate at 0° C. and 0.1 MPa: mL/sec) is preferably in the range of 0.1 to 100 g·sec/NmL, and more preferably about 5 to 50 g·sec/NmL. The total flow of the starting material gas in this case refers to the total of the flow of the chlorine-containing compound and fluorinating agent, and the flow of, when used, inert gas, molecular chlorine, oxygen, etc.

Reaction Product

According to the above-described method, the fluorination reaction of the above starting compound results in production of a fluoroolefin represented by formula (6): $CF_3(CF_2)_nCA=CHB$ wherein one of A and B is F, and the other is H, n is an integer of 0 to 2, proviso that n is 0 when a chlorine-containing alkene represented by formula (5) is used as a starting material, with a high starting material conversion and a good selectivity.

More specifically, when the starting material is at least one chlorine-containing compound selected from the group consisting of a chlorine-containing alkane represented by formula (1): $CX_3(CX_2)_nCClYCH_2Z$, a chlorine-containing alkene represented by formula (3): $CX_3(CX_2)_nCCl=CH_2$, and a chlorine-containing alkene represented by formula (5): $CH_2XCCl=CX_2$, a compound of formula (6) wherein A is F, and B is H, that is, a compound of formula (6-1): $CF_3(CF_2)_nCF=CH_2$ can be obtained. The resulting product may also contain another fluoroolefin that is a compound of formula (6) wherein A is H, and B is F, that is, a fluoroolefin represented by formula (6-2): $CF_3(CF_2)_nCH=CHF$, in both of which, n is an integer of 0 to 2, proviso that n is 0 when a chlorine-containing alkene represented by formula (5) is used as a starting material. Further, when the starting material is at least one chlorine-containing compound selected from the group consisting of a chlorine-containing alkane represented by formula (2): $CX_3(CX_2)nCH_2CHX_2$ and a chlorine-containing alkene represented by formula (4): $CX_3(CX_2)nCH=CHX$, a compound of formula (6) wherein A is H, and B is F, that is, a fluoroolefin represented by formula (6-2): $CF_3(CF_2)_nCH=CHF$ wherein n is an integer of 0 to 2, can be obtained.

For example, when the starting material is a chlorine-containing alkane represented by formula (1) (e.g., $CF_3CHClCH_2Cl$ (HCFC-243 db) or $CF_3CFClCH_3$ (HCFC-244bb)), a chlorine-containing alkene represented by formula (3) (e.g., $CCl_3CCl=CH_2$ (HCO-1230xf) or $CF_3CCl=CH_2$ (HCFO-1233xf)), a chlorine-containing alkene represented by formula (5) (e.g., $CH_2ClCCl=CCl_2$ (HCO-1230xa)), or the like, 2,3,3,3-tetrafluoropropene represented by formula: $CF_3CF=CH_2$ (HFO-1234yf) can be obtained. The resulting product may also contain 1,3,3,3-tetrafluoropropene represented by formula: $CF_3CH=CHF$ (HFO-1234ze), together with HFO-1234yf. Moreover, when the starting material is a chlorine-containing alkene represented by formula (4) (e.g., $CCl_3CH=CHCl$ (HCO-1230zd) or $CF_3CH=CHCl$ (HCFO-1233zd)), or the like, 1,3,3,3-tetrafluoropropene represented by formula: $CF_3CH=CHF$ (HFO-1234ze) can be obtained.

Furthermore, when the starting material is a mixture of at least one chlorine-containing compound selected from the group consisting of a chlorine-containing alkane represented by formula (1): $CX_3(CX_2)nCClYCH_2Z$, a chlorine-containing alkene represented by formula (3): $CX_3(CX_2)nCCl=CH_2$, and a chlorine-containing alkene represented by formula (5): $CH_2XCCl=CX_2$, and at least one chlorine-containing compound selected from the group consisting of a chlorine-containing alkane represented by formula (2): $CX_3(CX_2)nCH_2CHX_2$ and a chlorine-containing alkene represented by formula (4): $CX_3(CX_2)nCH=CHX$, a mixture of a fluoroolefin represented by formula (6-1) and a fluoroolefin represented by formula (6-2) can be obtained.

The reaction product can be recovered after purification by distillation or the like. Further, unreacted starting materials or intermediates obtained from the outlet of the reactor can be recycled by returning them to the reactor after separation and purification. Owing to the recycling of the unreacted starting materials, high productivity can be maintained even if the starting material conversion is not high.

In the production of 2,3,3,3-tetrafluoropropene (HFO-1234yf), 1,1,1,2,2-pentafluoropropane (HFC-245cb), which is a main component of the by-product contained in the product, can be easily converted into 2,3,3,3-tetrafluoropropene (HFO-1234yf) by hydrogen fluoride-elimination reaction; therefore, 1,1,1,2,2-pentafluoropropane (HFC-245cb) contained in the product is also a useful compound. Moreover, in the production of 1,3,3,3-tetrafluoropropene (HFO-1234ze), 1,1,1,3,3-pentafluoropropane (HFC-245fa), which is a main component of the by-product contained in the product, can be easily converted into 1,3,3,3-tetrafluoropropene (HFO-1234ze) by hydrogen fluoride-elimination reaction; therefore, 1,1,1,3,3-pentafluoropropane (HFC-245fa) contained in the product is also a useful compound.

Advantageous Effects of Invention

According to the method of the present invention, the target fluoroolefin can be obtained with a high starting material conversion and a good selectivity by using a chlorine-containing compound represented by a specific general formula as a starting material in the presence of a specific catalyst that is at least one member selected from the group consisting of chromium oxide containing a Group 5 element and fluorinated chromium oxide containing a Group 5 element. In particular, when the catalyst is chromium oxide containing two or more elements selected from the group consisting of V, Nb, and Ta, or fluorinated chromium oxide containing two or more elements selected from the group consisting of V, Nb, and Ta, the conversion of the starting material is further enhanced, and the selectivity of the target fluoroolefin is also increased, while catalyst degradation can be prevented, thereby allowing efficient production of the fluoroolefin.

Therefore, the method of the present invention is industrially advantageous as a method for producing fluoroolefins by fluorination of chlorine-containing compounds.

DESCRIPTION OF EMBODIMENTS

The present invention is described in more detail below with reference to Production Examples of catalysts used in the present invention, and Examples of the present invention.

Production Example 1

Preparation of Chromium Oxide Catalyst Precursor

10% aqueous ammonia (118 g) was added to 900 g of an aqueous solution in which 77 g of chromium nitrate nonahydrate was dissolved to precipitate chromium hydroxide by neutralization. The chromium hydroxide precipitate was taken by filtration with a Buchner funnel, and washed with deionized water, thereby obtaining chromium hydroxide.

Production Example 2

Preparation of Niobium-Containing Chromium Oxide Catalyst: Impregnation Method

A chromium hydroxide precipitate (300 g; weight in wet state after washing) prepared in the same manner as in Production Example 1 was added to an aqueous solution of niobium salt prepared by dissolving 3.1 g of ammonium niobium oxalate in 200 cc of water to form a slurry. The slurry was heated while stirring to evaporate water, and the obtained solid was dried at 120° C. for 12 hours. After grinding the solid into a powder, graphite was added in an amount of 3% based on the total weight, and the resulting mixture was molded into pellets ($\phi$ 2 mm×2 mm) and baked at 400° C. in a nitrogen flow, thereby obtaining niobium-containing chromium oxide.

The SEM analysis of the niobium-containing chromium oxide indicated that the atomic ratio of chromium to niobium was about 96:4, and that the composition of the oxide was approximately represented by $Cr_{0.96}Nb_{0.04}O_{2.02}$. Moreover, the XRD pattern of the oxide showed that the oxide was amorphous.

Production Example 3

Preparation of Niobium-Containing Chromium Oxide Catalyst: Coprecipitation Method A chromium-niobium ethanol solution obtained by dissolving 20.9 g of chromium nitrate and 1.78 g of niobium chloride (chromium:niobium (molar ratio)=90:10) in 105 mL of ethanol was added dropwise to a solution obtained by dissolving 65.0 g of ammonium acetate and 15.0 g of 25% aqueous ammonia in 1 L of water.

The produced precipitate was recovered by centrifugation and filtration, and the recovered product was washed with deionized water. These separation and washing procedures were repeated to recover the precipitate. The recovered precipitate was dried at 120° C. for 12 hours, and baked at 700° C. or more in an air atmosphere, thereby obtaining niobium-containing chromium oxide. The SEM analysis of the obtained niobium-containing chromium oxide indicated that the chromium/niobium atomic ratio was 90:10, and that the composition of the oxide was approximately represented by $Cr_{0.90}Nb_{0.10}O_{2.05}$.

The XRD pattern of the above niobium-containing chromium oxide catalyst after baking showed that the catalyst contained crystalline chromium oxide and crystalline niobium oxide, and that non-crystallized niobium and chromium were dispersed in the catalyst and present as amorphous oxides.

Production Example 4

Preparation of Niobium-Containing Chromium Oxide Catalyst: Coprecipitation Method A chromium-niobium ethanol solution obtained by dissolving 20.9 g of chromium nitrate and 0.89 g of niobium chloride (chromium:niobium (molar ratio)=95:5) in 105 mL of ethanol was added dropwise to a solution obtained by dissolving 65.0 g of ammonium acetate and 15.0 g of 25% aqueous ammonia in 1 L of deionized water.

The produced precipitate was recovered by centrifugation and filtration, and the recovered precipitate was washed with deionized water. These separation and washing procedures were repeated to recover the precipitate. The recovered precipitate was dried at 120° C. for 12 hours, and baked at 700° C. or more in an air atmosphere, thereby obtaining niobium-containing chromium oxide. The SEM analysis of the obtained niobium-containing chromium oxide indicated that the chromium/niobium atomic ratio was 95:5, and that the composition of the oxide was approximately represented by $Cr_{0.95}Nb_{0.05}O_{2.03}$.

The XRD pattern of the above niobium-containing chromium oxide catalyst after baking showed that the catalyst contained crystalline chromium oxide, and that niobium was amorphous and dispersed in the catalyst.

Example 1

The chromium oxide catalyst (10.0 g) containing 4 atom % of niobium based on the total metal atoms' prepared in Production Example 2 was placed in a 1 m-long tubular Hastelloy reactor.

The reactor was heated, and the catalyst was first fluorinated with hydrogen fluoride gas.

Subsequently, the temperature of the reactor was raised to 350° C., and anhydrous hydrogen fluoride gas and oxygen gas were supplied to the reactor at flow rates of 60.0 NmL/min and 0.6 NmL/min, respectively, and maintained for 0.5 hours. Thereafter, $CF_3CCl=CH_2$ (HCFC-1233xf) gas was supplied at a flow rate of 6.0 NmL/min. About 30 hours later, the effluent gas from the reactor was analyzed by gas chromatograph.

Table 1 shows the results. Since HFC-245cb in the product is a useful compound that can be converted into HFO-1234yf by hydrogen fluoride-elimination reaction, Table 1 also shows the total selectivity of HFO-1234yf and HFC-245cb. In addition, Table 1 shows the total yield of HFO-1234yf and HFC-245cb based on the starting material, calculated on the basis of the starting material conversion and the total selectivity of HFO-1234yf and HFC-245cb.

The symbols shown in the tables indicate the following compounds:
1233xf $CF_3CCl=CH_2$
1234yf $CF_3CF=CH_2$
245cb $CF_3CF_2CH_3$
1234ze $CF_3CH=CHF$
1233zd $CF_3CH=CHCl$ Example 2

The fluorination treatment of the catalyst and fluorination reaction were performed as in Example 1, except that the catalyst used was changed to the chromium oxide containing 10 atom % of niobium based on the total metal atoms prepared in Production Example 3. [shows the results.

Comparative Example 1

The chromium hydroxide obtained in Production Example 1 was dried at 120° C. for 12 hours, and the solid was ground into a powder. Then, graphite was added in an amount of 3% based on the total weight, and the resulting mixture was molded into pellets (φ 2 mm×2 mm) and baked at 400° C. in a nitrogen flow, thereby obtaining chromium oxide.

The fluorination treatment of the catalyst and fluorination reaction were performed as in Example 1, except that the obtained chromium oxide was used as the catalyst. Table 1 shows the results.

TABLE 1

|  | Ex. 1 | Ex. 2 | Comp. Ex. 1 |
| --- | --- | --- | --- |
| Catalyst production example | Prod. Ex. 2 | Prod. Ex. 3 | — |
| Group 5 element added | Nb | Nb | — |
| Cr/Group 5 element atomic ratio | 96:4 | 90:10 | 100:0 |
| X-ray diffraction results | Amorphous | Crystalline | Amorphous |
| 1233xf conversion (GC %) | 21 | 24 | 17 |
| 1234yf selectivity (GC %) | 67 | 67 | 66 |
| 245cb selectivity (GC %) | 23 | 28 | 23 |
| 1234ze selectivity (GC %) | 2 | 2 | 3 |
| 1233zd selectivity (GC %) | 1 | 1 | 1 |
| Other by-product selectivity (GC %) | 7 | 2 | 7 |
| 1234yf + 245cb selectivity (GC %) | 90 | 95 | 89 |
| 1234yf + 245cb total yield (%) | 19 | 23 | 15 |

As is clear from Table 1, when the fluorinated chromium oxide containing niobium was used as the catalyst, the total yield of HFO-1234yf and HFC-245cb was higher than that of Comparative Example 1, which used a chromium oxide catalyst. The results demonstrate that the target fluoroolefin can be obtained with a high starting material conversion and a good selectivity by using chromium oxide containing a Group 5 element or fluorinated chromium oxide containing a Group 5 element as the catalyst.

Example 3

The fluorination reaction is performed as in Example 2, except that the starting material is changed to $CF_3CH=CHCl$ (HCFO-1233zd).

As a result, the HCFO-1233zd conversion is 95%, and $CF_3CH=CHF$ (HFO-1234ze) at a selectivity of 86% and $CF_3CH_2CHF_2$ (HFC-245fa) at a selectivity of 13% are obtained as products. The total yield of HFO-1234ze and HFC-245fa based on HCFO-1233zd is 94%.

Comparative Example 2

The fluorination reaction is performed as in Comparative Example 1, except that the starting material is changed to $CF_3CH=CHCl$ (HCFO-1233zd).

As a result, the HCFO-1233zd conversion is 86%, and $CF_3CH=CHF$ (HFO-1234ze) at a selectivity of 85% and $CF_3CH_2CHF_2$ (HFC-245fa) at a selectivity of 13% are obtained as products. The total yield of HFO-1234ze and HFC-245fa based on HCFO-1233zd is 84%, which is lower than that of Example 3.

Production Example 5

Preparation of Chromium Oxide Catalyst Containing 1 Atom % of Vanadium

An aqueous solution (200 ml) in which 0.2 g of ammonium metavanadate was dissolved was added and mixed with 300 g of chromium hydroxide obtained in the same manner as in Production Example 1. The slurry was heated while stirring occasionally to evaporate water.

The remaining slurry was dried at 120° C., and the obtained solid was ground into a powder. Graphite was added in an amount of 3% based on the total weight, and the resulting mixture was molded into pellets (φ 2 mm×2 mm) and baked at 400° C. in a nitrogen flow, thereby obtaining vanadium-containing chromium oxide.

The SEM analysis of the oxide indicated that the atomic ratio of chromium and vanadium was about 99:1, and that the composition of the oxide was approximately represented by $Cr_{0.99}V_{0.01}O_{2.01}$. Further, according to the XRD of the oxide powder, no diffraction peak derived from the crystals of the oxide was observed, and the oxide was thus amorphous.

Production Example 6

Preparation of Chromium Oxide Catalyst Containing 6 Atom % of Vanadium

Vanadium-containing chromium oxide was obtained as in Production Example 5, except that the amount of ammonium metavanadate used was changed to 1.2 g.

The SEM analysis of the oxide indicated that the atomic ratio of chromium and vanadium was about 94:6, and that the composition of the oxide was approximately represented by $Cr_{0.94}V_{0.06}O_{2.03}$. Further, according to the XRD of the oxide powder, no diffraction peak derived from the crystals of the oxide was observed, and the oxide was thus amorphous.

Example 4

The chromium oxide catalyst (10.0 g) containing 1 atom % of vanadium prepared in Production Example 5 was placed in a 1 m-long tubular Hastelloy reactor.

The reactor was heated, and the catalyst was first fluorinated with hydrogen fluoride gas.

Subsequently, the temperature of the reactor was raised to 350° C., and anhydrous hydrogen fluoride gas and oxygen gas were supplied to the reactor at flow rates of 60.0 NmL/min and 0.12 NmL/min, respectively. Thereafter, $CF_3CCl=CH_2$ (HCFC-1233xf) gas was supplied at a flow rate of 6.00 NmL/min. In this case, the flow rate of oxygen gas supplied was 0.02 mol per mol of the starting material gas. About 100 hours later, the effluent gas from the reactor was analyzed by gas chromatograph.

Table 2 shows the results. Since HFC-245cb in the product is a useful compound that can be converted into HFO-1234yf by hydrogen fluoride-elimination reaction, Table 2 also shows the total selectivity of HFO-1234yf and HFC-245cb. In addition, Table 2 shows the total yield of HFO-1234yf and HFC-245cb based on the starting material, calculated on the basis of the starting material conversion and the total selectivity of HFO-1234yf and HFC-245cb.

Table 2 also shows the reduction rate of starting material conversion determined as a slope of a straight line connecting three points of a starting material conversion in the measurement point and starting material conversions 5 hours before and after the measurement point.

Example 5

The fluorination treatment of the catalyst and fluorination reaction were performed as in Example 4, except that the flow rate of oxygen gas supplied was changed to 0.60 NmL/min (0.1 mol per mol of the starting material gas). Table 2 shows the results.

Example 6

The fluorination treatment of the catalyst and fluorination reaction were performed as in Example 4, except that the catalyst used was changed to the chromium oxide containing 6 atom % of vanadium prepared in Production Example 6. Table 2 shows the results.

Example 7

The fluorination treatment of the catalyst and fluorination reaction were performed as in Example 4, except that the catalyst used was changed to the chromium oxide containing 6 atom % of vanadium prepared in Production Example 6, and that the flow rate of oxygen gas supplied was changed to 0.60 NmL/min (0.1 mol per mol of the starting material gas). Table 2 shows the results.

Comparative Example 3

The chromium hydroxide obtained in Production Example 1 was dried at 120° C., and the obtained solid was ground into a powder. Then, graphite was added in an amount of 3% based on the total weight, and the resulting mixture was molded into pellets (φ 2 mm×2 mm) and baked at 400° C. in a nitrogen flow, thereby obtaining chromium oxide.

The fluorination treatment of the catalyst and fluorination reaction were performed as in Example 4, except that the obtained chromium oxide was used as the catalyst. Table 2 shows the results.

TABLE 2

|  | Ex. 4 | Ex. 5 | Ex. 6 | Ex. 7 | Comp. Ex. 3 |
|---|---|---|---|---|---|
| Catalyst production example | Prod. Ex. 5 | Prod. Ex. 5 | Prod. Ex. 6 | Prod. Ex. 6 | — |
| Cr/V atomic ratio | 99:1 | 99:1 | 94:6 | 94:6 | 100:0 |
| $O_2$ gas supply (moles per mole of starting material) | 0.02 | 0.1 | 0.02 | 0.1 | 0.02 |

TABLE 2-continued

|  | Ex. 4 | Ex. 5 | Ex. 6 | Ex. 7 | Comp. Ex. 3 |
|---|---|---|---|---|---|
| 1233xf conversion (GC %) | 17 | 17 | 17 | 22 | 14 |
| 1234yf selectivity (GC %) | 66 | 66 | 61 | 56 | 67 |
| 245cb selectivity (GC %) | 23 | 23 | 21 | 19 | 23 |
| 1234ze selectivity (GC %) | 3 | 3 | 2 | 2 | 3 |
| 1233zd selectivity (GC %) | 1 | 1 | 1 | 1 | 1 |
| Other by-product selectivity (GC %) | 7 | 7 | 15 | 22 | 6 |
| 1234yf + 245cb selectivity (GC %) | 89 | 89 | 82 | 75 | 90 |
| 1234yf + 245cb total yield (%) | 15 | 15 | 14 | 17 | 13 |
| Conversion reduction rate (GC %/hr) | 0.00 | 0.00 | 0.00 | 0.00 | −0.05 |

As is clear from Table 2, when fluorinated chromium oxide containing vanadium was used as the catalyst (Examples 4 to 7), the starting material conversion was improved, and the total yield of HFO-1234yf and HFC-245cb was higher, as compared with Comparative Example 3, which used a chromium oxide catalyst not containing vanadium. The results confirmed that in the case of using a catalyst having a vanadium content of 1 to 6 atom %, the effect of preventing a decrease in starting material conversion was obtained when the amount of oxygen gas supplied was in a range as very low as 0.02 to 0.1 mol per mol of the starting material. In particular, in Example 4, which used a fluorinated chromium oxide catalyst containing 1 atom % of vanadium based on the total metal atoms, a decrease in starting material conversion was prevented, and the selectivity of the target product was maintained at a high level by simply supplying oxygen gas in an amount as low as 0.02 mol per mol of the starting material. As is clear from these results, the use of a catalyst having a low vanadium content, and the addition of a relatively small amount of oxygen can achieve remarkable effects of preventing catalyst degradation, maintaining high levels of starting material conversion and selectivity, and avoiding adverse effects caused by the use of excess oxygen.

Example 8

The fluorination reaction is performed as in Example 5, except that the starting material is changed to $CF_3CH=CHCl$ (HCFO-1233zd).

As a result, the HCFO-1233zd conversion is 95%, and $CF_3CH=CHF$ (HFO-1234ze) at a selectivity of 86% and $CF_3CH_2CHF_2$ (HFC-245fa) at a selectivity of 13% are obtained as products.

At the time of the effluent gas analysis about 200 hours after the start of the reaction, the reduction rate of starting material conversion is 0.00 GC %/hr, and a decrease in catalytic activity is prevented.

Comparative Example 4

The fluorination reaction is performed as in Comparative Example 3, except that the starting material is changed to $CF_3CH=CHCl$ (HCFO-1233zd).

As a result, the HCFO-1233zd conversion is 89%, and $CF_3CH=CHF$ (HFO-1234ze) at a selectivity of 85% and $CF_3CH_2CHF_2$ (HFC-245fa) at a selectivity of 13% are obtained as products.

At the time of the effluent gas analysis about 200 hours after the start of the reaction, the reduction rate of starting material conversion is −0.05 GC %/hr, and a decrease in catalytic activity is observed.

Example 9

The fluorination reaction is performed as in Example 5, except that the starting material is changed to $CF_3CHClCH_2Cl$ (HCFC-243db).

As a result, the HCFC-243db conversion is 100%, and $CF_3CCl=CH_2$ (HFO-1233xf) at a selectivity of 80%, $CF_3CF=CH_2$ (HFO-1234yf) at a selectivity of 12%, and $CF_3CF_2CH_3$ (HFC-245cb) at a selectivity of 4% are obtained as products. When 243db and 1233xf are regarded as starting materials, the starting material conversion is 20%.

At the time of the effluent gas analysis about 100 hours after the start of the reaction, the reduction rate of starting material conversion is 0.00 GC %/hr, indicating that a decrease in catalytic activity is prevented.

Comparative Example 5

The fluorination reaction is performed as in Comparative Example 3, except that the starting material is changed to $CF_3CHClCH_2Cl$ (HCFC-243db).

As a result, the HCFC-243db conversion is 100%, and $CF_3CCl=CH_2$ (HFO-1233xf) at a selectivity of 85%, $CF_3CF=CH_2$ (HFO-1234yf) at a selectivity of 10%, and $CF_3CF_2CH_3$ (HFC-245cb) at a selectivity of 3% are obtained as products. When 243db and 1233xf are regarded as starting materials, the starting material conversion is 15%.

At the time of the effluent gas analysis about 100 hours after the start of the reaction, the reduction rate of starting material conversion is −0.01 GC %/hr, indicating that a decrease in catalytic activity is prevented.

Production Example 7

Preparation of Nb- and V-Containing Chromium Oxide Catalyst: Coprecipitation Method An ethanol solution containing chromium, niobium, and vanadium obtained by dissolving 20.9 g of chromium nitrate, 1.5 g of niobium chloride, and 0.15 g of bis(2,4-pentanedionato)vanadium(IV) oxide in 105 mL of ethanol was added dropwise to a solution obtained by dissolving 65 g of ammonium acetate and 15.0 g of 25% aqueous ammonia in 1 L of water. This was repeated for two batches, and the produced precipitate was recovered by centrifugation and filtration. The recovered product was washed with deionized water. These separation and washing procedures were repeated to recover the precipitate.

The recovered precipitate was dried at 120° C., and then baked at 700° C. in an air atmosphere, thereby obtaining niobium- and vanadium-containing chromium oxide. The SEM analysis of the obtained niobium- and vanadium-containing chromium oxide indicated that the chromium/niobium/vanadium atomic ratio was 92.2:7.2:0.6, and that the composition of the oxide was approximately represented by $Cr_{0.922}Nb_{0.072}V_{0.006}O_{1.58}$.

The XRD pattern of the obtained Nb- and V-containing chromium oxide after baking confirmed that the Nb- and V-containing chromium oxide contained crystalline chromium oxide and crystalline complex oxide of chromium and niobium, while non-crystallized Nb and V were bonded to Cr, Nb and V via oxygen atoms and widely dispersed in the catalyst.

When the Nb- and V-containing chromium oxide obtained in the above manner was subjected to fluorination of a chlorine-containing compound, the obtained solid was ground into a powder, then graphite was added in an amount of 3% based on the total weight, and the resulting mixture was molded into pellets (φ 2 mm×2 mm) before use.

Production Example 8

Preparation of Nb- and V-Containing Chromium Oxide Catalyst: Coprecipitation Method 10% aqueous ammonia (130 g) was added dropwise to an ethanol aqueous solution containing chromium, niobium, and vanadium obtained by dissolving 76.8 g of chromium nitrate nonahydrate, 5.8 g of niobium chloride, and 0.57 g of bis(2,4-pentanedionato)vanadium(IV) oxide in 620 mL of water and 380 mL of ethanol.

The produced precipitate of chromium-niobium-vanadium hydroxide was taken by filtration and washed with deionized water. The precipitate was dried at 120° C., and then baked at 700° C. in an air atmosphere, thereby obtaining niobium- and vanadium-containing chromium oxide.

The SEM analysis of the obtained niobium- and vanadium-containing chromium oxide indicated that the chromium/niobium/vanadium atomic ratio was 89:10:1, and that the composition of the oxide was approximately represented by $Cr_{0.89}Nb_{0.10}V_{0.01}O_{1.61}$.

The XRD pattern of the Nb- and V-containing chromium oxide after baking showed that the niobium- and vanadium-containing chromium oxide after baking contained crystalline chromium oxide and crystalline complex oxide of chromium and niobium.

When used as the catalyst, the chromium oxide was molded before use as in Production Example 7.

Production Example 9

Preparation of Nb- and V-Containing Chromium Oxide Catalyst: Coprecipitation Method 10% aqueous ammonia (134 g) was added dropwise to an ethanol aqueous solution containing chromium, niobium, and vanadium obtained by dissolving 76.8 g of chromium nitrate nonahydrate, 5.8 g of niobium chloride, and 1.70 g of bis(2,4-pentanedionato)vanadium(IV) oxide in 620 mL of water and 380 mL of ethanol.

The produced precipitate of chromium-niobium-vanadium hydroxide was taken by filtration and washed with deionized water. The precipitate was dried at 120° C., and then baked at 700° C. in an air atmosphere, thereby obtaining niobium- and vanadium-containing chromium oxide.

The SEM analysis of the obtained niobium- and vanadium-containing chromium oxide indicated that the chromium/niobium/vanadium atomic ratio was 87:10:3, and that the composition of the oxide was approximately represented by $Cr_{0.87}Nb_{0.10}V_{0.03}O_{1.63}$.

The XRD pattern of the Nb- and V-containing chromium oxide after baking showed that the niobium- and vanadium-containing chromium oxide after baking contained crystalline chromium oxide and crystalline complex oxide of chromium and niobium.

When used as the catalyst, the chromium oxide was molded before use as in Production Example 7.

Production Example 10

Preparation of Crystalline Chromium Oxide

10% aqueous ammonia (118 g) was added to 900 g of an aqueous solution in which 77 g of chromium nitrate nonahydrate was dissolved to precipitate chromium hydroxide by neutralization. The obtained chromium hydroxide precipitate was taken by filtration, followed by washing with deionized water and filtration, thereby obtaining chromium hydroxide. The chromium hydroxide was dried at 120° C.

The obtained solid was ground into a powder and baked at 700° C. in an air flow, thereby obtaining chromium oxide.

The XRD pattern of the chromium oxide after baking showed that the chromium oxide after baking contained crystalline chromium oxide.

When used as the catalyst, the chromium oxide was molded before use as in Production Example 7.

Production Example 11

Preparation of Vanadium-Containing Chromium Oxide Catalyst: Coprecipitation Method 10% aqueous ammonia (122 g) was added dropwise to an ethanol aqueous solution containing chromium and vanadium obtained by dissolving 85.3 g of chromium nitrate nonahydrate and 0.57 g of bis(2,4-pentanedionato)vanadium(IV) oxide in 620 mL of water and 380 mL of ethanol.

The produced precipitate of chromium-vanadium hydroxide was taken by filtration and washed with deionized water. The precipitate was dried at 120° C., and then baked at 700° C. in an air atmosphere, thereby obtaining vanadium-containing chromium oxide. The SEM analysis of the obtained vanadium-containing chromium oxide indicated that the chromium/vanadium atomic ratio was 99:1, and that the composition of the oxide was approximately represented by $Cr_{0.99}V_{0.01}O_{1.51}$.

The XRD pattern of the vanadium-containing chromium oxide after baking showed that the vanadium-containing chromium oxide after baking contained crystalline chromium oxide. Since the amount of V-derived substances was low, no patterns indicating crystallinity appeared; however, due to the preparation by coprecipitation method, vanadium formed a complex oxide with chromium via oxygen, and the complex oxide was dispersed in the catalyst.

When used as the catalyst, the chromium oxide was molded before use as in Production Example 7.

Production Example 12

Preparation of Niobium-Containing Chromium Oxide Catalyst: Coprecipitation Method 10% aqueous ammonia (128 g) was added dropwise to an ethanol aqueous solution containing chromium and niobium obtained by dissolving 76.8 g of chromium nitrate nonahydrate and 5.8 g of niobium(V) chloride in 620 mL of water and 380 mL of ethanol.

The produced precipitate of chromium-niobium hydroxide was taken by filtration, and washed with deionized water. The precipitate was dried at 120° C., and then baked at 700° C. in an air atmosphere, thereby obtaining niobium-containing chromium oxide. The SEM analysis of the obtained niobium-containing chromium oxide indicated that the chromium/niobium atomic ratio was 90:10, and that the composition of the oxide was approximately represented by $Cr_{0.9}Nb_{0.1}O_{1.6}$.

The XRD pattern of the niobium-containing chromium oxide after baking showed that the niobium-containing chromium oxide after baking contained crystalline chromium oxide and crystalline complex oxide of chromium and niobium.

When used as the catalyst, the chromium oxide was molded before use as in Production Example 7.

Example 10

The Nb- and V-containing chromium oxide (7 g) prepared in Production Example 7 was placed in a 75 cm-long tubular Hastelloy reactor.

The reactor was heated, and hydrogen fluoride gas was introduced to fluorinate the above chromium oxide.

Subsequently, the temperature of the reactor was raised to 350° C. Anhydrous hydrogen fluoride gas, oxygen gas, and $CF_3CCl=CH_2$ (HCFC-1233xf) gas were supplied at flow rates of 42 NmL/min, 0.42 NmL/min, and 4.2 NmL/min, respectively, and the fluorination reaction of $CF_3CCl=CH_2$ (HCFC-1233xf) was performed. The effluent gas from the reactor was analyzed by gas chromatograph.

Table 3 shows the results. Since HFC-245cb in the product is a useful compound that can be converted into HFO-1234yf by hydrogen fluoride-elimination reaction, Table 3 also shows the total selectivity of HFO-1234yf and HFC-245cb. In addition, Table 3 shows the total yield of HFO-1234yf and HFC-245cb based on the starting material, calculated on the basis of the starting material conversion and the total selectivity of HFO-1234yf and HFC-245cb.

Example 11

The fluorination treatment of the catalyst and fluorination reaction were performed as in Example 10, except that the flow rate of oxygen gas was changed to 0.08 NmL/min. Table 3 shows the results.

Example 12

The fluorination treatment of the catalyst and fluorination reaction were performed as in Example 10, except that the catalyst used was changed to the Nb- and V-containing chromium oxide prepared in Production Example 8. Table 3 shows the results.

Example 13

The fluorination treatment of the catalyst and fluorination reaction were performed as in Example 10, except that the catalyst used was changed to the Nb- and V-containing chromium oxide catalyst prepared in Production Example 9. Table 3 shows the results.

Example 14

The fluorination treatment of the catalyst and fluorination reaction were performed as in Example 13, except that the flow rate of oxygen gas was changed to 0.08 NmL/min. Table 3 shows the results.

Comparative Example 6

The fluorination treatment of the catalyst and fluorination reaction were performed as in Production Example 10, except that the catalyst used was changed to the chromium oxide prepared in Production Example 10. Table 4 shows the results.

Example 15

The fluorination treatment of the catalyst and fluorination reaction were performed as in Example 10, except that the catalyst used was changed to the chromium oxide containing vanadium prepared in Production Example 11. Table 4 shows the results.

Example 16

The fluorination treatment of the catalyst and fluorination reaction were performed as in Example 10, except that the catalyst used was changed to the chromium oxide containing niobium prepared in Production Example 12. Table 4 shows the results.

TABLE 3

|  | Ex. 10 | Ex. 11 | Ex. 12 | Ex. 13 | Ex. 14 |
|---|---|---|---|---|---|
| Catalyst production example | Prod. Ex. 7 | | Prod. Ex. 8 | Prod. Ex. 9 | |
| Cr/Nb/V atomic ratio | 92.2:7.2:0.6 | | 89:10:1 | 87:10:3 | |
| X-ray diffraction results | Crystalline | | Crystalline | Crystalline | |
| Amount of $O_2$ (mol/%-1233xf) | 10 | 2 | 10 | 10 | 2 |
| 1233xf conversion (GC %) | 35.5 | 35.6 | 28.4 | 26.8 | 26.6 |
| 1234yf selectivity (GC %) | 67.8 | 67.8 | 67.5 | 66.2 | 67.8 |
| 245cb selectivity (GC %) | 26.8 | 27.5 | 26.3 | 25.7 | 25.5 |
| 1234ze selectivity (GC %) | 1.70 | 1.95 | 1.41 | 0.90 | 1.17 |
| 1233zd selectivity (GC %) | 0.71 | 0.80 | 0.62 | 0.48 | 0.51 |
| $CO_2$ selectivity (GC %) | 0.32 | 0.15 | 0.33 | 1.02 | 0.44 |
| Other by-product selectivity (GC %) | 2.67 | 1.80 | 3.84 | 5.70 | 4.58 |
| 1234yf + 245cb selectivity (GC %) | 94.6 | 95.3 | 93.5 | 91.9 | 93.3 |
| 1234yf + 245cb total yield (%) | 33.6 | 33.9 | 26.6 | 24.6 | 24.8 |

TABLE 4

|  | Comp. Ex. 6 | Ex. 15 | Ex. 16 |
|---|---|---|---|
| Catalyst production example | Prod. Ex. 10 | Prod. Ex. 11 | Prod. Ex. 12 |
| Cr/Nb/V atomic ratio | — | 99:0:1 | 90:10:0 |
| X-ray diffraction results | Crystalline | Crystalline | Crystalline |
| Amount of $O_2$ (mol/%-1233xf) | 10 | 10 | 10 |
| 1233xf conversion (GC %) | 20.0 | 25.6 | 25.4 |
| 1234yf selectivity (GC %) | 68.0 | 57.2 | 69.5 |
| 245cb selectivity (GC %) | 23.0 | 22.9 | 24.7 |
| 1234ze selectivity (GC %) | 4.3 | 1.05 | 1.70 |
| 1233zd selectivity (GC %) | 1.3 | 0.56 | 0.65 |
| $CO_2$ selectivity (GC %) | 0.9 | 8.4 | 0.20 |
| Other by-product selectivity (GC %) | 2.5 | 9.89 | 3.25 |
| 1234yf + 245cb selectivity (GC %) | 91.0 | 80.1 | 94.2 |
| 1234yf + 245cb total yield (%) | 18.0 | 20.5 | 23.9 |

As is clear from the results shown in Tables 3 and 4, when chromium oxide containing Nb and V was used as the catalyst, the total yield of HFO-1234yf and HFC-245cb was higher than that of Comparative Example 6, which used a chromium oxide catalyst.

Examples 15 and 16 show the results of the cases in which chromium oxide containing either one of V and Nb was used as the catalyst, and the total yield of HFO-1234yf and HFC-245cb was higher than that of Comparative Example 6. In Examples 10 to 14, which show the results of the cases in which chromium oxide containing both V and Nb was used as the catalyst, the total yield of HFO-1234yf and HFC-245cb was higher than that of Examples 15 and 16.

Moreover, as shown in Examples 11 and 14, when chromium oxide containing Nb and V was used as the catalyst, activity deterioration was suppressed, and high starting material conversion was obtained, even under conditions where the amount of oxygen, which was added to prevent the deterioration, was as very low as 2 mol % based on the starting material. These results demonstrate that the target fluoroolefin can be obtained with a high starting material conversion and a good selectivity by using chromium oxide containing Nb and V, or fluorinated chromium oxide containing Nb and V as the catalyst.

The invention claimed is:

1. A process for producing a fluoroolefin of the following formula (6): $CF_3(CF_2)_nCA\!=\!CHB$, wherein one of A and B is F and the other is H, n is an integer of 0 to 2, with the proviso that n is 0 when a chlorine-containing alkene of the formula (5) is used as a starting material, the method comprising reacting, in a vapor phase, a fluorinating agent and at least one chlorine-containing compound in the presence of at least one catalyst selected from the group consisting of chromium oxide containing a Group 5B element and fluorinated chromium oxide containing a Group 5B element, wherein the at least one chlorine-containing compound is selected from the group consisting of a chlorine-containing alkane of the following formula (1): $CX_3(CX_2)_n CClYCH_2Z$, wherein X is independently F or Cl, Y is H or F, when Y is H, Z is Cl or F, and when Y is F, Z is H, and n is an integer of 0 to 2; a chlorine-containing alkane of the following formula (2): $CX_3(CX_2)_n CH_2CHX_2$, wherein X is independently F or Cl, and at least one X is Cl, and n is an integer of 0 to 2; a chlorine-containing alkene of the following formula (3): $CX_3(CX_2)_n CCl\!=\!CH_2$, wherein X is independently F or Cl, and n is an integer of 0 to 2; a chlorine-containing alkene of the following formula (4): $CX_3(CX_2)_n CH\!=\!CHX$, wherein X is independently F or Cl, and at least one X is Cl, and n is an integer of 0 to 2; and the chlorine-containing alkene of the following formula (5): $CH_2XCCl\!=\!CX_2$, wherein X is independently F or Cl, and wherein the Group 5B element is in a quadrivalent or pentavalent state.

2. The process for producing a fluoroolefin according to claim 1, wherein the Group 5B element contained in the catalyst is at least one element selected from the group consisting of V and Nb.

3. The process for producing a fluoroolefin according to claim 1, wherein the Group 5B element contained in the catalyst is two or more elements selected from the group consisting of V, Nb, and Ta.

4. The process for producing a fluoroolefin according to claim 1, wherein the Group 5B element in the catalyst is contained in an amount of 0.1 to 30 atom % based on the total amount of Cr and the Group 5B element in the catalyst.

5. The process for producing a fluoroolefin according to claim 1, wherein the catalyst contains vanadium in an amount of 0.1 to 6 atom % based on the total amount of Cr and the Group 5B element in the catalyst.

6. The process for producing a fluoroolefin according to claim 1, wherein the fluorinating agent is anhydrous hydrogen fluoride.

7. The process for producing a fluoroolefin according to claim 1, wherein the chlorine-containing compound used as a starting material is at least one member selected from the group consisting of the chlorine-containing alkane of the following formula (1): $CX_3(CX_2)_n CClYCH_2Z$, the chlorine-containing alkene of the following formula (3): $CX_3(CX_2)_n CCl\!=\!CH_2$, and the chlorine-containing alkene of the following formula (5): $CH_2XCCl\!=\!CX_2$, and the fluoroolefin obtained is a compound of the following formula (6-1): $CF_3(CF_2)_n CF\!=\!CH_2$, or a mixture of the compound of the formula (6-1) and a compound of the following formula (6 2): $CF_3(CF_2)_n CH\!=\!CHF$, wherein n in each of formula (6-1) and formula (6-2) is an integer of 0 to 2, with the proviso that n is 0 when the chlorine-containing alkene of the formula (5) is used as a starting material.

8. The process for producing a fluoroolefin according to claim 7, wherein the chlorine-containing compound used as a starting material is at least one member selected from the group consisting of $CF_3CHClCH_2Cl$ (HCFC-243db), $CF_3CFClCH_3$ (HCFC-244bb), $CCl_3CCl\!=\!CH_2$ (HCO-1230xf), $CF_3CCl\!=\!CH_2$ (HCFO-1233xf), and $CH_2ClCCl\!=\!CCl_2$ (HCO-1230xa), and the fluoroolefin obtained is $CF_3CF\!=\!CH_2$ (HFO-1234yf) or a mixture of $CF_3CF\!=\!CH_2$ (HFO-1234yf) and $CF_3CH\!=\!CHF$ (HFO-1234ze).

9. The process for producing a fluoroolefin according to claim 1, wherein the chlorine-containing compound used as a starting material is at least one member selected from the group consisting of the chlorine-containing alkane of the following formula (2): $CX_3(CX_2)_n CH_2CHX_2$ and the chlorine-containing alkene of the following formula (4): $CX_3(CX_2)_n CH\!=\!CHX$, and the fluoroolefin obtained is a fluoroolefin of the following formula (6-2): $CF_3(CF_2)_n CH\!=\!CHF$, wherein n is an integer of 0 to 2.

10. The process for producing a fluoroolefin according to claim 9, wherein the chlorine-containing compound used as a starting material is at least one member selected from the group consisting of $CCl_3CH\!=\!CHCl$ (HCO-1230zd) and $CF_3CH\!=\!CHCl$ (HCFO-1233zd), and the fluoroolefin obtained is $CF_3CH\!=\!CHF$ (HFO-1234ze).

11. The process for producing a fluoroolefin according to claim 10, wherein the chlorine-containing compound used as a starting material is $CF_3CH\!=\!CHCl$ (HCFO-1233zd) and the fluoroolefin obtained is $CF_3CH\!=\!CHF$ (HFO-1234ze).

12. The process for producing a fluoroolefin according to claim 1, wherein reaction is performed in the presence of oxygen, chlorine, or both oxygen and chlorine.

13. The process for producing a fluoroolefin according to claim 12, wherein the reaction is performed in the presence of oxygen in an amount of 0.001 to 0.2 mol per mol of the chlorine-containing compound used as a starting material.

* * * * *